(12) United States Patent
Kuri

(10) Patent No.: US 8,360,957 B2
(45) Date of Patent: Jan. 29, 2013

(54) METHOD OF TREATING ERECTILE DYSFUNCTION

(76) Inventor: Yamil Kuri, Miami, FL (US)

( * ) Notice: Subject to any disclaimer, the term of this patent is extended or adjusted under 35 U.S.C. 154(b) by 372 days.

(21) Appl. No.: 12/423,743

(22) Filed: Apr. 14, 2009

(65) Prior Publication Data

US 2009/0264700 A1 Oct. 22, 2009

Related U.S. Application Data

(60) Provisional application No. 61/124,311, filed on Apr. 16, 2008.

(51) Int. Cl.
*A61F 5/00* (2006.01)
(52) U.S. Cl. .......................................................... 600/38
(58) Field of Classification Search ................ 600/38–41
See application file for complete search history.

(56) References Cited

U.S. PATENT DOCUMENTS

| | | | |
|---|---|---|---|
| 4,643,175 A | 2/1987 | Chapman | |
| 4,989,592 A | 2/1991 | Chang | |
| 5,085,209 A | 2/1992 | Gottschalk | |
| 5,158,556 A | 10/1992 | Starley | |
| 5,218,974 A | 6/1993 | Garrett | |
| 5,221,251 A | 6/1993 | Edminster | |
| 5,244,454 A | 9/1993 | Coates | |
| 5,270,323 A | 12/1993 | Milne, Jr. et al. | |
| 5,583,144 A | 12/1996 | Kral | |
| 5,728,043 A | 3/1998 | Yong | |
| 5,855,548 A | 1/1999 | Place | |
| 5,893,827 A | 4/1999 | Jaquez et al. | |
| 6,061,840 A | 5/2000 | Alligator | |
| 6,309,344 B1 | 10/2001 | Werner | |
| 6,390,095 B1 | 5/2002 | Magnusson | |
| 7,341,553 B2 | 3/2008 | Egretier | |
| 2002/0094988 A1 | 7/2002 | Hines et al. | |
| 2008/0119690 A1* | 5/2008 | Comeau | 600/39 |
| 2009/0209807 A1* | 8/2009 | Kozak et al. | 600/38 |

* cited by examiner

*Primary Examiner* — John Lacyk
(74) *Attorney, Agent, or Firm* — Jacqueline Tadros, P.A.

(57) ABSTRACT

The present invention is a novel method of using an elastic band comprising a tubular member constructed in the form of a closed loop, to restrict the flow of blood to the corpora cavernosa, resulting in occlusion of the dorsal veins in the penis and allowing blood to be trapped in the corpus cavernosum to enhance sexual performance and treat erectile dysfunction.

3 Claims, 1 Drawing Sheet

METHOD OF TREATING ERECTILE DYSFUNCTION

CROSS-REFERENCE TO RELATED APPLICATIONS

Applicant claims priority from Provisional Patent Application No. 61/124,311 filed on Apr. 16, 2008 and entitled "Device for enhancing and maintaining an erection of the penis" under Title 35, United States Code Section 119(e). An entire copy of Provisional Patent Application No. 61/124,311 is incorporated herein by reference.

TECHNICAL FIELD OF THE INVENTION

The present invention relates generally to a method of enhancing and maintaining an erection and more particularly to a method of treating erectile dysfunction, including but not limited to, erectile dysfunction attributable to venous leak conditions.

BACKGROUND OF THE INVENTION

Erectile dysfunction, also known as ED is the inability to achieve or sustain an adequate erection for sexual activity. Viagra®, Levitra® and Cialis® are three drugs that are often the first course of treatment tried for all variations of erectile dysfunction. In addition to drug treatment, numerous other approaches have been developed to treat ED, including for example, hormone therapy and surgery, including vascular reconstructive surgery.

Vasculogenic (arterial or venous) is one classification of erectile dysfunction disorder. Venous conditions explain the majority of erectile dysfunctions in patients with normal arterial anatomy. The venous leak is characterized by the absence of a sustainable erection, no increase of the intra-cavernous pressure and a rapid opacification of venous plexus under a normal perfusion flow. Venous leak conditions result from a failure of adequate venous occlusion.

The process of achieving and sustaining an erection depends on the proper functioning of the nervous system, corpus cavernosal arteries, corpus cavernosum tissue, tunica albuginea tissue and occlusion of veins in the penis. If any of these areas of the body are not functioning or are not completely functional, this can cause erectile dysfunction.

Erectile dysfunction may sometimes be remedied by restricting the outflow of blood from the corpora cavernosa in order to maintain an erection. The reduction in venous blood flow, known as venous occlusion, allows blood to be trapped in the corpus cavernosum. This process continues until the pressure in the corpus cavernosum equals the pressure of the corpus cavernosal arteries. It is at this point that the penis is fully erect.

A number of devices have also been invented to assist in the treatment of erectile dysfunction by restricting blood from the corpora cavernosa in order to maintain an erection. However, many of the devices are cumbersome and inconvenient to use.

Drug treatment and surgery are often expensive and involve a certain degree of risk and health consequences. Thus, it would be advantageous to have a viable option for the treatment of ED that also circumvents the use of drugs and avoids the need for surgery and is also simple and easy to implement.

SUMMARY OF THE INVENTION

The present invention relates generally to a method of enhancing and maintaining an erection and more particularly to a method of treating erectile dysfunction, including but not limited to, erectile dysfunction attributable to venous leak conditions.

The invention utilizes an elastic band comprising a tubular member constructed in the form of a closed loop. The tubular member comprises a stretchable material that is capable of retaining its original length after being stretched.

The elastic tubular member may be fabricated from a stretchable latex, silicone rubber, thermoplastic rubber or similar material of circular or oval cross-section.

The elastic band is around the waist from the front and encircles below the buttocks from behind. The band is pulled from under the scrotum, between the legs and is engaged at the top upper surface base of the penis when erect.

The pressure applied at the top base of the penis can be easily adjusted. For adjustment, the elastic band is loosened or stretched tight along the sides of the scrotum and buttocks where the material of the tubular member grips itself to the skin by virtue of snug friction to hold the desired pressure.

The elastic band which is adjustable without the use of a clamp or other fastening devices will serve comfortably and easily to enhance and maintain an erection of the penis.

The method of the present invention is simple and easy to implement so as not to interfere with a user's comfort and enjoyment. Some of the objects, features and advantages of the present invention are outlined hereunder.

An object of the method of the present invention is to provide a means of enhancing and maintaining an erection and treating erectile dysfunction, including but not limited to, erectile dysfunction attributable to venous leak conditions without resorting to drug therapy or surgical procedures.

It is an object of the present invention to provide a blood flow-restricting method to treat erectile dysfunction.

It is a further object of the invention to provide a simplified, minimally disruptive method that does not require cumbersome apparatus and may be used to treat and accommodate all body types.

An advantage of the present invention is that it offers ease of use and does not require further assembly by the end-user. Another advantage of the method of the present invention is that it provides a highly cost effective treatment for erectile dysfunction There has thus been outlined, rather broadly, the more important features of the invention in order that the detailed description thereof may be better understood and in order that the present contribution to the art may be better appreciated.

These as well as additional advantages of the present invention will become apparent of the following detailed description of the present invention when read in light of the several figures.

DETAILED DESCRIPTION OF THE INVENTION

Figure 1:
FIG. 1 is a top view of the tubular member constructed to form a closed loop

Referring now to the drawings, FIG. 1 shows an elastic band 10 comprising a tubular member 12 constructed in the form of a closed loop. The tubular member 12 comprises a stretchable material that clings well to skin and is capable of retaining its original shape and length after being stretched.

The elastic tubular member may be fabricated from a stretchable latex, silicone rubber, thermoplastic rubber or similar material of circular or oval cross-section.

The tubing may be manufactured from any number of materials. Preferred materials for tubing include, thermoplastic rubber, surgical or latex rubber as well as synthetic elastomers, such as silicones and copolymers well known in the art.

Additional materials will be readily apparent to those skilled in the art. Tubing structures formed from such materials may be fabricated using conventional techniques, such as, compression, transfer or injection molding procedures.

Figure 2:
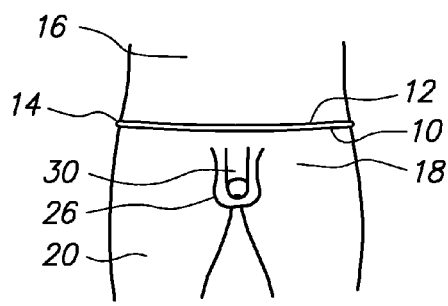
FIG. 2 is a front view of the user's stomach, pelvic region and upper thighs with the tubular member placed about the user's waist.

The elastic band 10 is placed around a user's waist 14 from the front and encircling below the user's buttocks 24 from behind. FIG. 2 shows a front view of the user's stomach 16 pelvic region 18 and upper thighs 20 with the tubular member 12 placed about the user's waist 14.

Figure 3:
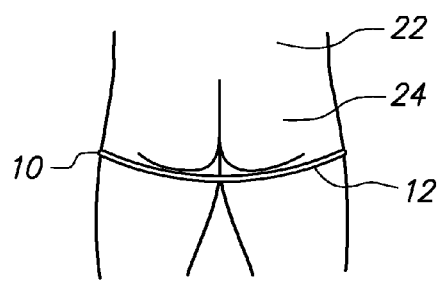
FIG. 3 is a view of the user's back and buttocks with the tubular member encircling the bottom of the buttocks.
Figure 4:
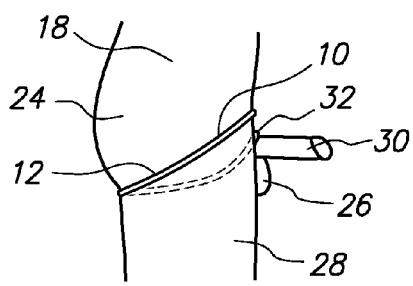
FIG. 4 is a side view of a male's pelvic region with the tubular member encircling the bottom of the buttocks.

FIG. 3 is a view of the user's back 22 and buttocks 24 with the tubular member 12 encircling the bottom of the buttocks 24. FIG. 4 is a side view of a male's pelvic 18 region with the tubular member 12 encircling the bottom of the buttocks 24.

The elastic band 10 is pulled from under the user's scrotum 26 and up between the user's legs 28 in order to engage the user's penis 30 at a top upper surface base 32 of the penis 30 when erect.

Figure 5:
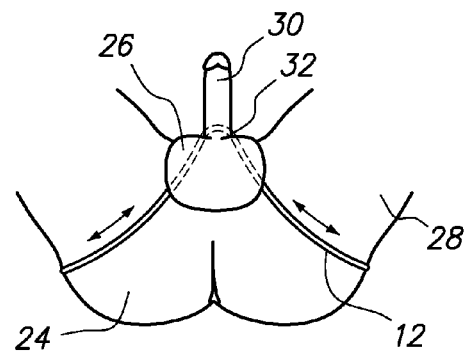
FIG. 5 is a bottom view of the user's buttocks with the tubular member encircling the bottom of the buttocks pulled and engaged at the upper surface base of the penis

FIG. 5 is a bottom view of the user's buttocks 24 with the tubular member 12 encircling the bottom of the buttocks 24 pulled and engaged at the upper surface base 32 of the penis 30 when erect at a top upper surface base 32 over the dorsal veins of the penis.

Figure 6:
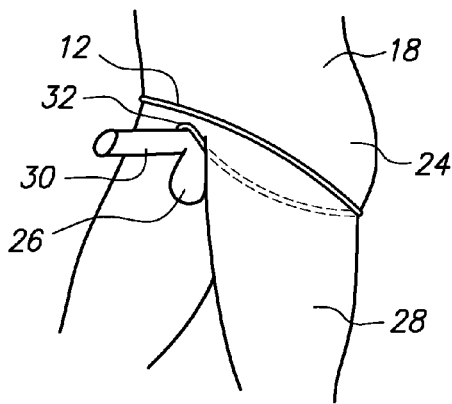
FIG. 6 is a side perspective view of a male's pelvic region with the tubular member pulled down from behind to encircle the bottom of the buttocks and engaged at the upper surface base of the penis.

FIG. 6 is a side perspective view of a male's pelvic region 18 with the tubular member 12 encircling the bottom of the buttocks 24 and engaged at the upper surface base 32 of the penis 30.

The pressure applied at the top upper surface base 32 of the penis 30 can be easily adjusted. For adjustment, the elastic band 10 is loosened or stretched tight along the sides of the scrotum 26 and buttocks 24 where the material of the tubular member grips itself to the skin by virtue of snug friction to hold the desired pressure as shown in FIG. 5.

The elastic band 10 which is adjustable without the use of a clamp or other fastening devices will serve comfortably and easily to enhance and maintain an erection of the penis 30.

Figure 7:
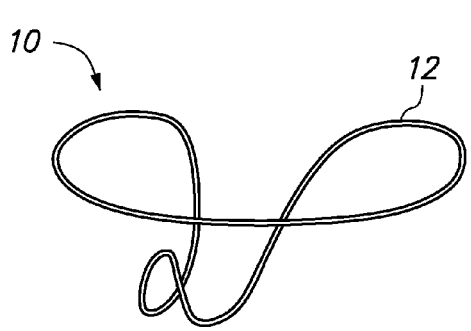
FIG. 7 is a top view showing the form of tubular member properly adjusted when in use.

FIG. 7 is a top view showing the form of tubular member 12 properly adjusted when in use.

Failure of the venous occlusive mechanism can allow blood to drain away during an erection rather than be held in the erectile tissue. This will prevent the build up of pressure necessary for an erection to be sustained.

The elastic band 10 is pulled tightly along the sides of the scrotum 26 and buttocks 24 as shown in FIG. 5. The band 10 is gripped in position when it clings to the skin. The non-allergenic material of the elastic band 10 adheres closely to the skin via snug friction.

The tightening of the elastic band 10 by a user when it is in proper position as shown in FIGS. 5 and 6 will restrict the flow of blood and result in occlusion of the dorsal veins in the penis. The reduction in venous blood flow, known as venous occlusion, allows blood to be trapped in the corpus cavernosum. This process continues until the pressure in the corpus cavernosum equals the pressure of the corpus cavernosal arteries. It is at this point that the penis is fully erect and the erection is sustained.

Thus the method of the present invention can aid in enhancing and maintaining an erection and aid in the treatment of erectile dysfunction as well as producing an improvement in patients with impotence due to venous leaks.

While the invention has thus been described with some degree of particularity, it is understood that this description has been given only by way of example and that numerous changes in the details of construction, fabrication and use, including the combination and arrangement of parts, may be made without departing from the spirit and scope of the invention.

I claim:

1. A method of treating erectile dysfunction, said method comprising the steps of:
(a) providing a single elastic band comprising a single tubular member constructed in the form of a continuous homogeneous closed loop, wherein said tubular member comprises a stretchable material that adheres to human skin and is capable of retaining its original shape and length after being stretched and wherein said length is sufficient to encircle a male waist; (b) placing said elastic band around a male waist and positioning said elastic band to encircle below the male buttocks; (c) pulling said elastic band from under the scrotum and up between the male's upper thighs to engage the male penis when erect at a top upper surface base over the dorsal veins of the penis; (d) pulling said elastic band in a direction along the sides of the scrotum and buttocks to tighten said elastic band and restrict the flow of blood resulting in occlusion of the dorsal veins in the penis to temporarily desensitize the dorsal nerves at the base and (e) repeating step 1(d) to adjust the pressure as necessary to maintain the penile erection.

2. A method of treating erectile dysfunction, said method comprising the steps of:
(a) providing a single elastic band comprising a single tubular member constructed in the form of a continuous homogeneous closed loop, wherein said tubular member comprises an oval cross section of a stretchable material that adheres to human skin and is capable of retaining its original shape and length after being stretched and wherein said length is sufficient to encircle a male waist; (b) placing said elastic band around a male waist and positioning said elastic band to encircle below the male buttocks; (c) pulling said elastic band from under the scrotum and up between the male's upper thighs to engage the male penis when erect at a top upper surface base over the dorsal veins of the penis; (d) pulling said elastic band in a direction along the sides of the scrotum and buttocks to tighten said elastic band and restrict the flow of blood resulting in occlusion of the dorsal veins in the penis to temporarily desensitize the dorsal nerves at the base and (e) repeating step 2(d) to adjust the pressure as necessary to maintain the penile erection.

3. A method of treating erectile dysfunction, said method comprising the steps of:
(a) providing a single elastic band comprising a single tubular member constructed in the form of a continuous homogeneous closed loop, wherein said tubular member comprises a circular cross section of a stretchable material that adheres to human skin and is capable of retaining its original shape and length after being stretched and wherein said length is sufficient to encircle a male waist; (b) placing said elastic band around a male waist and positioning said elastic band to encircle below the male buttocks; (c) pulling said elastic band from under the scrotum and up between the male's upper thighs to engage the male penis when erect at a top upper surface base over the dorsal veins of the penis; (d) pulling said elastic band in a direction along the sides of the scrotum and buttocks to tighten said elastic band and restrict the flow of blood resulting in occlusion of the dorsal veins in the penis to temporarily desensitize the dorsal nerves at the base and (e) repeating step 3(d) to adjust the pressure as necessary to maintain the penile erection.

* * * * *